United States Patent [19]

Albrecht et al.

[11] 4,411,905
[45] Oct. 25, 1983

[54] ANTISECRETORY 1,2,4-TRIAZOLE-3-THIOLS

[75] Inventors: William L. Albrecht; Winton D. Jones, both of Cincinnati, Ohio

[73] Assignee: Richardson-Merrell Inc., Cincinnati, Ohio

[21] Appl. No.: 273,531

[22] Filed: Jun. 15, 1981

Related U.S. Application Data

[60] Continuation of Ser. No. 143,456, Apr. 24, 1980, abandoned, which is a division of Ser. No. 71,814, Sep. 4, 1979, Pat. No. 4,230,715.

[51] Int. Cl.$^3$ .................... A61K 31/41; C07D 249/12
[52] U.S. Cl. .................................. 424/269; 424/232; 548/263; 548/479
[58] Field of Search ............... 548/263, 265; 424/269, 424/232

[56] References Cited

U.S. PATENT DOCUMENTS 3,954,981  5/1976  Albrecht et al. .................... 424/246

FOREIGN PATENT DOCUMENTS 866648  11/1978  Belgium ........................... 548/263
1620506  2/1970  Fed. Rep. of Germany ...... 424/269

OTHER PUBLICATIONS

Ainsworth et al., J. Am. Chem. Soc. 75, 4915-4918 (1953).
Artemov et al., Chem. Abstracts 76:34220f (1972).

*Primary Examiner*—Alton D. Rollins
*Attorney, Agent, or Firm*—Edlyn S. Simmons; Gary D. Street; William J. Stein

[57] ABSTRACT

Compounds of the formula

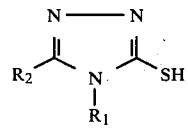

wherein $R_1$ is H or $NH_2$;
$R_2$ is $C_{1-6}$ straight or branched chain alkyl; —$CH_2OH$; —$(CH_2)_n$—O—$(CH_2)_m$—$CH_3$; phenyl; or —$(CH_2)_p NH_2$;
n is 1-3;
m is 0-3; and
p is 1-5;

and the pharmaceutically acceptable acid addition salts of those compounds of basic character, have antisecretory activity.

2 Claims, No Drawings

ANTISECRETORY 1,2,4-TRIAZOLE-3-THIOLS

This is a continuation of application Ser. No. 143,456 filed Apr. 24, 1980 now abandoned which is a division of of application Ser. No. 71,814 filed Sept. 4, 1979 now U.S. Pat. No. 4,230,715.

BACKGROUND OF THE INVENTION

The present invention relates to 1,2,4-triazole-3-thiols having antisecretory activity.

Many 1,2,4-triazole-3-thiols are known. For example, a class of such compounds has been tested for antiinflammatory and analgesic activity (George et al, J. Med. Chem. 14(4), 335–8 (1971)). Others have been tested for antitubercular, diuretic, natriuretic or goitrogenic activity (Yale et al, J. Med. Chem. 9(1), 42–6 (1966); Hartmann et al, Rev. soc. argentina biol. 30, 87–96; and Hoggarth et al, Brit. J. Pharmacol. 6, 454–8 (1951)). They are also known as photographic developing agents (Japanese Pat. No. 73 34, 174; U.S. Pat. No. 3,901,709; U.S. Pat. No. 3,576,629; and U.S. Pat. No. 3,666,471); metal complexing agents (German Pat. No. 2,331,220); pigments (U.S. Pat. No. 3,681,374); and additives in printing inks (German Pat. No. 2,215,474). Many such compounds have also been synthesized, (e.g., Willems et al, Bull. Soc. Chem. Belges 75 (5–6), 358–65 (1966)) and utilized as chemical intermediates (e.g., Niebch et al, Z. Naturforsch, B 27 (6), 675–82 (1972) and Jones et al, J. Am. Chem. Soc. 77, 1538–40 (1955)). Additionally, they are reported as having other pharmacological activities, e.g., antitumor (Hahn et al, J. Nat. Cancer Inst. 48 (3), 783–90 (1972)), radioprotectant (German Pat. No. 2,021,453), antihepatotoxic (Rauen et al, Arzneim-Forsch 23 (1a), 141–5 (1973)) and as an antidote against nitrogen mustard (German Pat. No. 2,021,453). Related structures are also known to have hypoglycemic activity (Deliwala et al, J. Med. Chem. 14 (3), 260–2 (1971)). However, this class of compounds is not known as antisecretory agents.

SUMMARY OF THE INVENTION

Compounds of the following Formula I

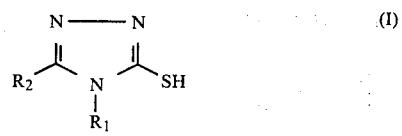

wherein
$R_1$ is H or $NH_2$;
$R_2$ is $C_{1-6}$ straight or branched chain alkyl; —$CH_2OH$; —$(CH_2)_n$—O—$(CH_2)_m$—$CH_3$; phenyl; or —$(CH_2)_p NH_2$;
n is 1-3;
m is 0-3; and
p is 1-5;
and the pharmaceutically acceptable acid addition salts of those compounds of basic character are useful as antisecretory agents.

DETAILED DESCRIPTION OF THE INVENTION

Illustrative examples of straight or branched chain $C_{1-6}$ alkyl groups which $R_2$ may represent as used herein include, for example, methyl, ethyl, n-propyl, isopropyl, n-butyl, sec-butyl, isobutyl, tert-butyl, n-pentyl, isopentyl, neopentyl, n-hexyl, isohexyl, etc.

Pharmaceutically acceptable acid addition salts of the compounds of Formula I possessing basic character include those of any suitable inorganic or organic acid. Suitable inorganic acids are, for example, hydrochloric, hydrobromic, sulfuric or phosphoric acid. Suitable organic acids are, for example, carboxylic acids, such as acetic, propionic, glycolic, lactic, pyruvic, malonic, succinic, fumaric, malic, tartaric, citric, ascorbic, maleic, hyroxymaleic, benzoic, hydroxybenzoic, phenylacetic, cinnamic, salicylic and 2-phenoxybenzoic, or sulfonic acids such as, for example, methanesulfonic and 2-hydroxyethanesulfonic acid.

Of the compounds of Formula I, the preferred compounds are those in which $R_2$ is alkyl, preferably $C_{1-4}$ alkyl, e.g., 4-amino-5-ethyl-4H-1,2,-4-triazole-3-thiol.

Illustrative examples of compounds of this invention include those wherein $R_1$ is $NH_2$. Specific compounds include, for example, 4-amino-5-methyl-4H-1,2,4-triazole-3-thiol, 4-amino-5-ethyl-4H-1,2,4-triazole-3-thiol, 4-amino-5-mercapto-4H-1,2,4-triazole-3-methanol, 4-amino-5-(methoxymethyl)-4H-1,2,4-triazole-3-thiol, 4-amino-5-propyl-4H-1,2,4-triazole-3-thiol, 4-amino-5-butyl-4H-1,2,4-triazole-3-thiol, 4-amino-5-ethoxymethyl-4H-1,2,4-triazole-3-thiol, 4-amino-5-phenyl-4H-1,2,4-triazole-3-thiol, 4-amino-5-(2-ethoxyethyl)-4H-1,2,4-triazole-3-thiol, 4-amino-5-(5-aminopentyl)-4H-1,2,4-triazole-3-thiol hydrochloride, 4-amino-5-(2-aminoethyl)-4H-1,2,4-triazole-3-thiol hydrochloride, and the 4-unsubstituted compounds corresponding to each of the foregoing, including 5-ethyl-1H-1,2,4-triazole-3-thiol and can be used, e.g., as adjunctive therapy for the treatement of peptic ulcer.

The compounds of this invention are useful as antisecretory agents. These compounds can be administered to warm-blooded animals, mammals, rats, mice, dogs, cats, horses, pigs, cows, sheep, and humans. As used herein, the term "patient" is intended to mean the animal or mammal being treated.

The antisecretory activity of the compounds of this invention may be illustrated by their effectiveness in standard pharmacological screening tests. For example, antisecretory efficacy may be demonstrated by inhibition of gastric acid secretion in rats (Shay Test: Shay et al, Gastroenterology 5:43, 1945). To illustrate such antisecretory utility, male Sprague-Dawley rats, weighing 200–250 g, were fasted for 48 hours prior to the experiment. They were allowed access to a 10% dextrose-0.5% sodium chloride solution during the fasting. The test compound in 0.5% methylcellulose solution was then injected intraduodenally below a ligation made around the duodenum at a site as close to the pyloric sphinctor as possible. After the incision was closed with wound clips, each rat was returned to its cage. Four hours later, the rats were sacrificed. Their stomachs were carefully excised and the amount of gastric acid in the gastric fluid was measured (mEq HCl/100 g of body weight). The acid output of the drug treated group is expressed as a percent of that of the vehicle group (%C). For 4-amino-5-propyl-4H-1,2,4-triazole-3-thiol, %C was 18%, and for 4-amino-5-butyl-4H-1,2,4-triazole-3-thiol, %C was 42%. The measured $ED_{50}$ for 4-amino-5-ethyl-4H-1,2,4-triazole-3-thiol was 3.4 mg/kg.

The compounds of this invention can be administered orally or parenterally either alone or in the form of a pharmaceutical preparation. Pharmaceutical preparations containing conventional pharmaceutical carriers and as active ingredients compounds of this invention can be employed in unit dosage forms such as solids, for example, tablets, capsules, and pills, or liquid solutions, suspensions, or emulsions for oral and parenteral administration. The dosage unit administered can be any antisecretorily effective amount. The quantity of compound administered can vary over a wide range to provide about 1–100, preferably about 1–25, mg/kg of body weight of the patient per day, to achieve the desired effect. Unit doses can contain about 5–300 mg of a compound of this invention and may be administered, for example, from 1 to 4 times daily.

The compounds of Formula I wherein $R_1$ is $NH_2$ and $R_2$ is alkyl, —$CH_2OH$, alkoxyalkyl or phenyl may be prepared by reacting thiocarbohydrazide

$$NH_2NHCNHNH_2$$

with a carboxylic acid of the formula $R_2COOH$ wherein $R_2$ has the values given above. The reaction is usually run neat as a melt or, optionally, in the presence of excess acid as solvent. The reaction temperature is generally 100°–170° C. and the reaction is normally run for 5–120 minutes.

The compound wherein $R_1$ is $NH_2$ and $R_2$ is phenyl preferably is prepared by reaction of methyl 2-benzoyl-dithiocarbazinate with hydrazine using the procedures described by Hoggarth, J. Chem. Soc., 4811 (1952).

The compounds wherein $R_1$ is $NH_2$ and $R_2$ is aminoalkyl may be prepared by essentially the same carboxylic acid/thiocarbohydrazide reaction described above except that the amino acid must be suitably protected and the amino-protecting group subsequently removed. Thus, for example, such compounds may be prepared by first reacting phthalic anhydride with the appropriate w-aminoalkanoic acid of the formula.

$NH_2(CH_2)_pCOOH$ at a temperature of 150°–180° C. (i.e., by fusion of the reactants) for 1–10 hours, thus preparing the corresponding phthalimidoalkanoic acid of the formula

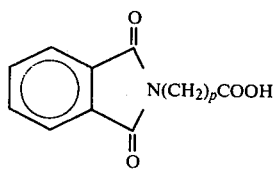

The latter acid is then reacted with thiocarbohydrazide again under fusion conditions (150°–180° C.) for 30 minutes-6 hours, producing the corresponding 5-(phthalimidoalkyl)-4-amino-4H-1,2,4-triazole-3-thiol of the formula

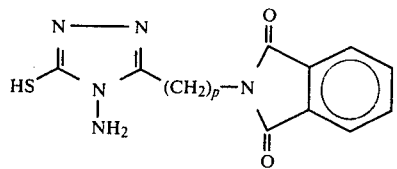

The latter compound is then reacted with hydrazine, e.g., hydrazine hydrate, in water at 25°–100° C. for 1–24 hours to remove the protecting group and produce the corresponding 5-(aminoalkyl)-4-amino-4H-1,2,4-triazole-3-thiol. The latter such compound wherein p is 5 may also be prepared by reacting O-methyl-caprolactam with thiocarbohydrazide analogously with the reaction of carboxylic acids with thiocarbohydrazide described herein (See also Example 9.)

The compounds of Formula I wherein $R_1$ is H may also be prepared by a reaction analogous to the above-described condensation of carboxylic acids with thiocarbohydrazide. For these $R_1=H$ compounds, the corresponding acid chloride of the formula $R_2COCl$ wherein $R_2$ is as defined above is reacted with thiosemicarbazide at a temperature of from 0° C. to room temperature and for a time of 24–72 hours in, e.g., pyridine. The resulting substituted thiosemicarbazide is then heated in, e.g., sodium methoxide, at a temperature of from room temperature to the reflux temperature of methanol for a time of 4–24 hours. For the corresponding compounds wherein $R_2$ is aminoalkyl, the starting material amino acid chloride should have its amino group protected with, e.g., phthalimido, as described above.

EXAMPLES

The following examples are illustrative of the invention.

EXAMPLE 1

4-Amino-5-(2-ethoxyethyl)-4H-1,2,4-triazole-3-thiol 63.6 g (0.6 mole) of thiocarbohydrazide and 100.0 g (0.85 mole) of 3-ethoxypropionic acid are stirred and heated at reflux until solution is achieved. The resultant solution is cooled to room temperature, diluted with 700 ml of diethyl ether and refrigerated for 1 hour. The crude white solid (94.6 g) when filtered and recrystallized from 1200 ml of water, gives 54.6 g of lustrous white plates of 4-amino-5-(2-ethoxyethyl)-4H-1,2,4-triazole-3-thiol. m.p. 123°–124° C.

EXAMPLES 2–7

Using the procedures of EXAMPLE 1, thiocarbohydrazide is reacted with acetic acid, propionic acid, methoxyacetic acid, buturic acid, valeric acid and ethoxyacetic acid to produce, respectively, 4-amino-5-methyl-4H-1,2,4-triazole-3-thiol (m.p. 209°–211° C.), 4-amino-5-ethyl-4H-1,2,4-triazole-3-thiol (m.p. 149°–150° C.), 4-amino-5-(methoxymethyl)-4H-1,2,4-triazole-3-thiol, (m.p. 123°–124° C.), 4-amino-5-propyl-4H-1,2,4-triazole-3-thiol (m.p. 105°–107° C.), 4-amino-5-butyl-4H-1,2,4-triazole-3-thiol (m.p. 89°–90° C.), and 4-amino-5-(ethoxymethyl)-4H-1,2,4-triazole-3-thiol (m.p. 209°–210° C.).

EXAMPLE 8

4-Amino-5-mercapto-4H-1,2,4-triazole-3-methanol

A mixture of 10.6 g (0.1 mole) of thiocarbohydrazide and 25.0 g (0.33 mole) of hydroxyacetic acid were heated and stirred at 130° C. for 20 minutes. The mixture is cooled to room temperature and diluted with 25 ml of water. It is then cooled for 24 hours at 11° C., yielding 7.0 g of crystals. The latter are recrystallized from chloroform/methanol, affording 4.5 g of solvated product. The product is dried in vacuo, affording 2.0 g of pale yellow crystals of 4-amino-5-mercapto-4H-1,2,4-triazole-3-methanol. m.p. 150.5°–151.5° C. When the reaction is repeated, using a longer heating time, (1 hour at 125° C.), and is followed by recrystallization from methanol/water, a higher yield of the same product is obtained (80%).

EXAMPLE 9

4-Amino-5-(5-aminopentyl)-4H-1,2,4-triazole-3-thiol hydrochloride

To 200 ml of methanol is added 3.6 g (0.1 mole) of gaseous HCl followed by 12.7 g (0.1 mole) of O-methylcaprolactam and then 10.6 g (0.1 mole) of thiocarbohydrazide. After heating at reflux for 2 hours, the mixture is allowed to cool to room temperature and is refrigerated. The solid product is recrystallized twice from methanol/ethyl acetate, affording 13.4 g of 4-amino-5-(5-aminopentyl)-4H-1,2,4-triazole-3-thiol hydrochloride. m.p. 192°–194° C.

EXAMPLE 10

4-Amino-5-phenyl-4H-1,2,4-triazole-3-thiol 180 g of benzoylhydrazide, 135 g of carbon disulfide, 90 g of potassium hydroxide, 540 ml of ethanol and 120 ml of water are stirred together at room temperature for 1 hour. A yellow solid precipitates. This solid is redissolved by the addition of 120 ml of water. Methyl iodide is added to this aqueous solution at room temperature with stirring. The solution is then stirred for 30 minutes during which time a thick white precipitate is formed. The latter is filtered and air dried, yielding 125 g of methyl-2-benzoyl-dithiocarbazinate (m.p. 161°–169° C.). The latter solid is refluxed with methanol and hydrazine hydrate, yielding 4-amino-5-phenyl-4H-1,2,4-triazole-3-thiol. m.p. 194°–196° C.

EXAMPLE 11

4-Amino-5-(2-aminoethyl)-4H-1,2,4-triazole-3-thiol hydrochloride 1 mole of phthalic anhydride and 1 mole of β-alanine are fused at 170°–178° C. for 1½ hours in an open flask with stirring. The solution is allowed to stand overnight and solidifies. The resultant compound is crystallized from water producing phthalimidopropionic acid. 44 g (0.2 mole) of the latter is fused with 21.2 g (0.2 mole) of thiocarbohydrazide at 150±2° C. for 45 minutes. The molten mass is cooled and washed with 500 ml of water. It is then filtered and crystallized from ethanol. The product is recrystallized from acetic acid/water, yielding 11 g of 5-phthalimidoethyl)-4-amino-4H-1,2,4-thiazole-3-thiol. To a mixture of 10.0 g (0.034 mole) of the latter in 60 ml of water is added 10 ml of hydrazine hydrate (85%) (0.2 mole). After a few minutes, solution occurs. It is then stirred for two days. The solution is then placed in a refrigerator, yielding 2.5 g of the solid product. The solid is dissolved in methanol (200 ml), filtered and treated with ethereal HCl, yielding a precipitate. The latter is recrystallized from methanol/ethyl acetate and from ethanol, yielding 2.5 g of 4-amino-5-(2-aminoethyl)-4H-1,2,4-triazole-3-thiol hydrochloride. m.p. 230°–234° C.

EXAMPLE 12

5-Ethyl-1H-1,2,4-triazole-3-thiol 117 g (1.3 mole) of thiosemicarbazide and 120 g (1.3 moles) of propionyl chloride (added to the thiosemicarbazide in 1 liter of pyridine at 0° C.) are stirred in pyridine for 2½ days at room temperature. The pyridine is removed in vacuo. The residue is dissolved in 1 liter of methanol (dry) and treated with 2.6 moles of sodium methoxide. The mixture is refluxed for 8 hours and allowed to stand overnight at room temperature. Methanol is removed in vacuo and the residue is dissolved in water, cooled and made acidic with concentrated HCl. The resulting precipitate is filtered and air dried, yielding 160 g of a solid product. About 20 g of this product is recrystallized from methanol/water. The recrystallized solid is dried at 70° C. in vacuo for 24 hours, yielding 5-ethyl-1H-1,2,4-triazole-3-thiol. m.p. 259°–261° C.

EXAMPLE 13

An illustrative composition for tablets is as follows:

|  | Per Tablet |
| --- | --- |
| (a) 4-Amino-5-ethyl-4H—1,2,4-triazole-3-thiol | 100.0 mg |
| (b) Wheat starch | 15.0 mg |
| (c) Lactose | 33.5 mg |
| (d) Magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 14

An illustrative composition for a parenteral injection is the following wherein the quantities are on a weight to volume basis.

|  | Amount |
| --- | --- |
| (a) 4-Amino-5-ethyl-4H—1,2,4-triazole-3-thiol | 100.0 mg |
| (b) Sodium chloride | q.s. |
| (c) Water for injection to make | 20 ml |

The composition is prepared by dissolving the active ingredient (a) and sufficient sodium chloride in water for injection to render the solution isotonic. The composition may be dispensed in a single ampoule containing 100 mg of the active ingredient for multiple dosage or in 20 ampoules for single dosage.

EXAMPLE 15

An illustrative composition for hard gelatin capsules is as follows:

|  | Amount |
| --- | --- |
| (a) 4-Amino-5-ethyl-4H—1,2,4-triazole-3-thiol | 200.0 mg |

-continued

| | Amount |
|---|---|
| (b) Talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 16

An illustrative composition for pills is the following:

| | Per Pill |
|---|---|
| (a) 4-Amino-5-ethyl-4H—1,2,4-triazole-3-thiol | 200 mg |
| (b) Corn starch | 130 mg |
| (c) Liquid glucose | 20 ml |

The pills are prepared by blending the active ingredient (a) and the corn starch; then adding the liquid glucose with thorough kneading to form a plastic mass from which the pills are cut and formed.

I claim:

1. A pharmaceutical composition comprising in unit dosage form about 5-300 mg. of a compound of the formula

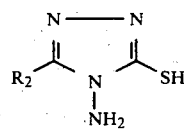

wherein $R_2$ is $-CH_2OH$ or $-(CH_2)_pNH_2$; and p is 1-5, or a pharmaceutically acceptable acid addition salt thereof and a significant amount of a pharmaceutically acceptable carrier.

2. A compound having the formula

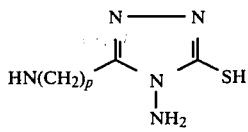

wherein p is 1-5; and the pharmaceutically acceptable acid addition salts thereof.

* * * * *